United States Patent
Pomeranz et al.

[11] Patent Number: 5,345,936
[45] Date of Patent: Sep. 13, 1994

[54] APPARATUS WITH BASKET ASSEMBLY FOR ENDOCARDIAL MAPPING

[75] Inventors: Mark L. Pomeranz, Los Gatos; Mir A. Imran, Palo Alto, both of Calif.

[73] Assignee: Cardiac Pathways Corporation, Sunnyvale, Calif.

[21] Appl. No.: 83,085

[22] Filed: Jun. 25, 1993

Related U.S. Application Data

[63] Continuation-in-part of Ser. No. 44,255, Apr. 7, 1993, which is a continuation-in-part of Ser. No. 983,968, Dec. 1, 1992, which is a continuation-in-part of Ser. No. 656,764, Feb. 15, 1991, Pat. No. 5,156,151.

[51] Int. Cl.$^5$ ............... A61B 5/04; A61N 1/05
[52] U.S. Cl. ............... 128/642; 607/122
[58] Field of Search ............... 128/642; 607/115, 116, 607/119, 122, 123, 126, 128, 130; 606/127, 198, 199, 200

[56] References Cited

U.S. PATENT DOCUMENTS

| | | | |
|---|---|---|---|
| 4,522,212 | 6/1985 | Gelinas et al. | 128/642 |
| 4,649,924 | 3/1987 | Taccardi | 128/642 |
| 4,681,564 | 7/1987 | Landreneau . | |
| 4,699,147 | 10/1987 | Chilson et al. | 128/642 |
| 4,940,064 | 7/1990 | Desai | 604/105 X |
| 5,010,894 | 4/1991 | Edhag | 607/119 |
| 5,156,151 | 10/1992 | Imran . | |

Primary Examiner—Lee S. Cohen
Assistant Examiner—Jeffrey R. Jastrzab
Attorney, Agent, or Firm—Flehr, Hohbach, Test, Albritton & Herbert

[57] ABSTRACT

An apparatus for mapping the wall of a chamber of the heart having blood therein. The apparatus includes a flexible elongate tubular member having proximal and distal extremities and at least one lumen extending therethrough. A basket assembly is carried by the distal extremity of the flexible elongate tubular member and is movable between contracted and expanded positions. The basket assembly has a plurality of elongate flexible circumferentially spaced-apart arms with proximal and distal extremities. A plurality of longitudinally spaced-apart electrodes are carried by each arm for engaging the wall of the heart. Spacing members coupled to the arms and extending between the arms are provided for establishing a desired substantially uniform circumferential spacing between the arms when the basket assembly is in expanded position in engagement with the wall of the heart. Openings are provided between the arms and the spacing members through which blood can flow.

15 Claims, 3 Drawing Sheets

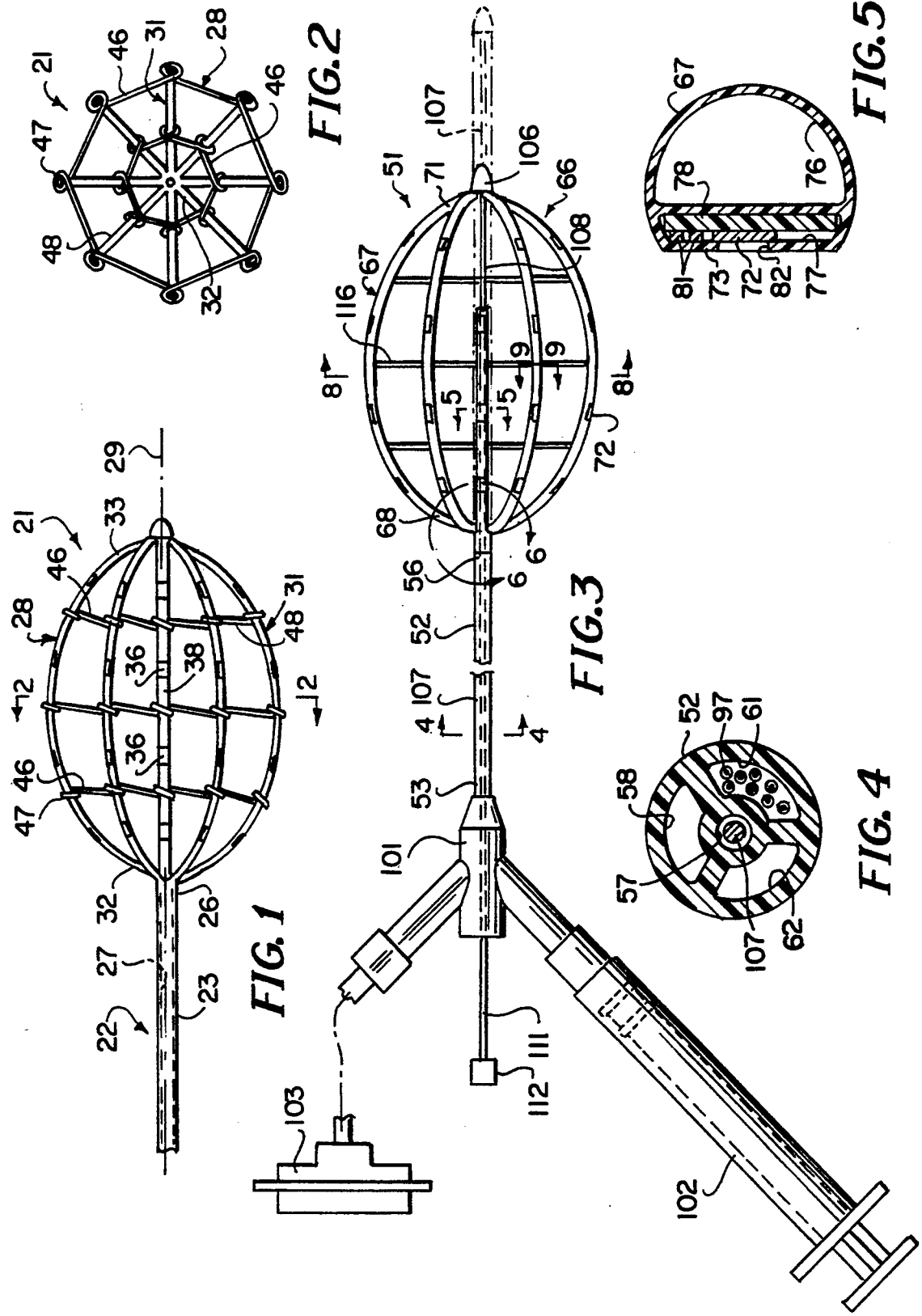

APPARATUS WITH BASKET ASSEMBLY FOR ENDOCARDIAL MAPPING

This application is a continuation-in-part of application Ser. No. 08/044,255 filed Apr. 7, 1993, which is a continuation-in-part of application Ser. No. 07/983,968 filed Dec. 1, 1992, which is a continuation-in-part of application Ser. No. 07/656,764 filed Feb. 15, 1991, now U.S. Pat. No. 5,156,151.

This invention pertains generally to medical apparatus for performing endocardial mapping and, more specifically, to endocardial mapping apparatus having a basket assembly with an array of electrodes thereon.

Catheters have been provided with basket assemblies on the distal end for performing endocardial mapping. These basket assemblies are formed from a plurality of elongate flexible arms which substantially engage the endocardium and permit blood in the heart to flow therethrough. In some of these basket assemblies, for example the basket assemblies of applications Ser. No. 08/044,255 filed Apr. 7, 1993, Ser. No. 07/983,968 filed Dec. 1, 1992 and Ser. No. 07/656,764 filed Feb. 15, 1991, there have been difficulties in maintaining the desired spacing of the arms during mapping due to the generally noncircular contour of the wall of the heart.

In general, it is an object of the present invention to provide a new and improved endocardial mapping apparatus which maintains substantially uniform circumferential spacing of the electrodes on the distal end thereof during endocardial mapping.

Another object of the invention is to provide an endocardial mapping apparatus of the above character in which a plurality of radially and longitudinally spaced electrodes are provided in a basket assembly which permits blood to flow therethrough during endocardial mapping.

Another object of the invention is to provide an endocardial mapping apparatus of the above character in which the array of electrodes are expanded into engagement with the wall of the chamber of the heart and are maintained in engagement with that wall during pumping action of the heart.

Another object of the invention is to provide an endocardial mapping apparatus of the above character in which the basket assembly is formed from a plurality of circumferentially spaced-apart arms having minimal mechanical resistance for permitting them to travel through tortuosities within the microcirculatory system of the patient.

These and other objects are achieved in accordance with the invention by an apparatus for mapping the wall of a chamber of the heart having blood therein. The apparatus includes a flexible elongate tubular member having proximal and distal extremities and at least one lumen extending therethrough. A basket assembly is carried by the distal extremity of the flexible elongate tubular member and is movable between contracted and expanded positions. The basket assembly has a plurality of elongate flexible circumferentially spaced-apart arms with proximal and distal extremities. A plurality of longitudinally spaced-apart electrodes are carried by each arm for engaging the wall of the heart. Spacing means coupled to the arms and extending between the arms is provided for establishing a desired substantially uniform circumferential spacing between the arms when the basket assembly is in expanded position in engagement with the wall of the heart. The spacing means has openings therebetween through which blood can flow.

FIG. 1 is a side elevational view of a portion of an endocardial mapping apparatus of the present invention.

FIG. 2 is a cross-sectional view taken along the line 2—2 of FIG. 1.

FIG. 3 is a side elevational view, partially sectioned and broken away, of an another embodiment of the endocardial mapping apparatus of the present invention.

FIG. 4 is a cross-sectional view taken along the line 4—4 of FIG. 3.

FIG. 5 is a cross-sectional view taken along the line 5—5 of FIG. 3.

Figure 6:
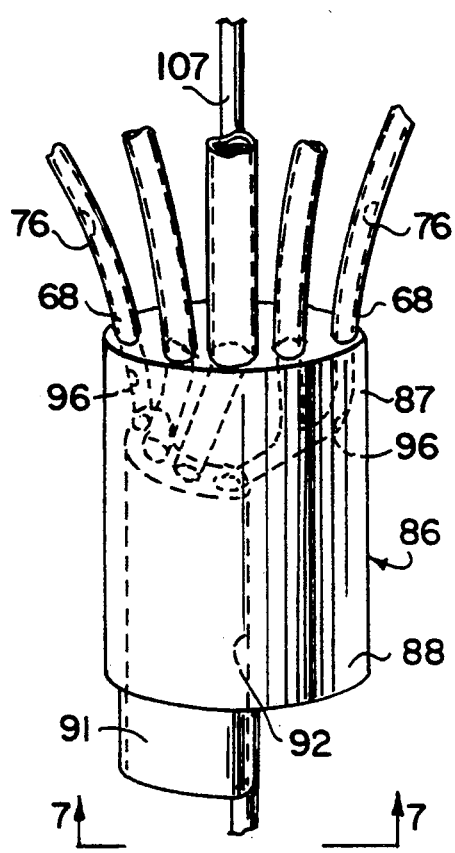
FIG. 6 is an enlarged view taken along the line 6—6 of FIG. 3 and rotated 90 degrees.

Apparatus 21 of the present invention is for mapping the wall of a chamber of the heart and includes a catheter probe 22 described in detail in application Ser. No. 08/044,255 filed Apr. 7, 1993. Briefly, catheter probe 22 has a flexible elongate tubular member 23 formed of a suitable material such as plastic which is circular in cross section and is provided with a proximal extremity, not shown in the drawings, and a distal extremity 26 (See FIG. 1). Tubular member 23 is provided with at least one lumen 27 extending therethrough from the proximal extremity to distal extremity 26 and carries a basket assembly 28 at distal extremity 26. Basket assembly 28 has a central longitudinal axis 29 and is moveable between contracted and expanded positions substantially therealong.

Expandable basket assembly 28 is provided with a plurality of, and as shown in the drawings eight, circumferentially spaced-apart longitudinally extending flexible arms 31 having joined proximal and distal extremities or end portions 32 and 33. Elongate flexible arms 31 have an outwardly bowed shaped memory and are each formed of an elastic band or member with a tube of a suitable insulating heat shrinkable material such as plastic slipped thereover and shrunk thereon by the application of heat. A plurality of longitudinally spaced-apart electrodes 36 are carried by each elongate flexible arm 31 for engaging the wall of the heart. More specifically, elongate flexible arms 31 each have an outer surface 38 facing outwardly from longitudinal axis 29 with a plurality of electrodes 36, and as shown in FIG. 1 four electrodes 36, disposed thereon. Elongate flexible arms 31 can also carry a plurality of longitudinally spaced-apart radiopaque markers or traces, not shown in the drawings, formed of a suitable material such as platinum or gold.

Endocardial mapping apparatus 21 includes a plurality of flexible members or fibers 46 made of any suitable material such as Kevlar and having a width or diameter ranging from 0.001 to 0.003 inches. Fibers 46 are coupled to elongate flexible arms 31 of catheter probe 22 to serve as cross-bracing and are included within the spacing means of mapping apparatus 21 for establishing a desired substantially uniform circumferential spacing between the elongate flexible arms when basket assembly 28 is in expanded position in engagement with the wall of the heart (See FIGS. 1 and 2). Fibers 46 extend between adjacent elongate flexible arms 31 at an angle with respect thereto and are mounted or attached to the elongate flexible arms in a plurality of locations spaced longitudinally between proximal and distal extremities 32 and 33. More specifically, fibers 46 wrap around each elongate flexible arm to form a loop 47 and are further secured thereto by any suitable adhesive, not shown in the drawings, which is compatible with the material of the elongate flexible arms. Three fibers 46 aligned at substantially right angles with respect to elongate flexible arms 31 when basket assembly 28 is in its expanded position are shown in FIG. 1 and form three annular rings spaced longitudinally along longitudinal axis 28. Fibers 46 and elongate flexible arms 31 form a plurality of openings 48 therebetween.

The operation of mapping apparatus 21 is similar to the operation of the endocardial mapping apparatus and system shown and described in applications Ser. No. 07/656,764 filed Feb. 15, 1991 and Ser. No. 08/044,255 filed Apr. 7, 1993. Briefly, an introducer sheath and a guiding catheter can be used to facilitate insertion of mapping apparatus 21 into a ventricle or other chamber of the heart for mapping of the endocardium therein. Once the guiding catheter has been advanced through the introducer sheath and the circulatory system of the patient to a valve of the heart, for example the aortic valve into the left ventricle of the heart, a pigtail catheter which has been preloaded into the guiding catheter is advanced out of the guiding catheter and through the aortic valve down to the apex of the ventricle. The guiding catheter is then slid over the pigtail catheter, the pigtail catheter removed from the guiding catheter and mapping apparatus 21 inserted through the guiding catheter until contracted basket assembly 28 fixed to distal extremity 26 of flexible elongate tubular member 23 reaches the tip of the guiding catheter. The guiding catheter is then pulled back across the aortic valve and flexible arms 31 of basket assembly 28 caused to expand so that electrodes 36 thereof substantially engage the wall of the heart for detecting electrical impulses or activity in the cells of the endocardium of the wall.

As discussed above, the generally noncircular cross-sectional contour of the ventricle or chamber of the heart tends to urge elongate flexible arms 31 out of their generally symmetrical circumferential spacing during mapping. Fibers 46 restrain elongate flexible arms 31 from pulling apart or moving away from an adjacent elongate flexible arm more than a predetermined distance generally equal to the length of the fiber interconnecting adjacent elongate flexible arms. The attachment means of a suitable adhesive and loops 47 inhibit fibers 46 from sliding down elongate flexible arms 31 during mapping. Openings 48 between elongate flexible arms 31 and fibers 46 permit blood to flow therethrough so that the operation of the heart is generally uninterrupted during mapping. The radiopaque markers permit fluoroscopic location and observation of basket assembly 28 within the chamber of the heart.

In another aspect of the invention illustrated in FIGS. 3 through 9, spacing means similar to fibers 46 can be used with catheter probes having a basket assembly formed of inflatable arms. The endocardial mapping apparatus, shown in FIG. 3, consists of a catheter probe 51 having a flexible elongate tubular member 52 formed of a suitable material such as plastic which is circular in cross section, as shown in FIG. 4. Flexible elongate tubular member 52 has a suitable diameter, as for example 0.080 to 0.130 inches, and a suitable length, as for example 100 to 150 centimeters, and is provided with proximal and distal extremities 53 and 56. At least one lumen and as shown in FIG. 4 first, second, third and fourth lumens 57, 58, 61 and 62 extend from proximal extremity 53 to distal extremity 56. First or central lumen 57 is a centrally disposed lumen which is generally circular in cross section and has a diameter ranging from 0.035 to 0.055 inches, and second or fluid conducting lumen 58 and third and fourth lumens 61 and 62 are generally crescent-shaped lumens circumferentially disposed around central lumen 57.

A flexible basket assembly 66 is secured in a fixed position to distal extremity 56 of flexible elongate tubular member 52 and is moveable between a contracted position, shown in dotted lines in FIG. 3, and an expanded position, shown in solid lines in FIG. 3. In its contracted position, basket assembly 66 has a length ranging from 6 to 12 centimeters and a width or diameter ranging from 0.08 to 0.15 inches. Basket assembly 66 is provided with a plurality of, and as shown in the drawings eight, circumferentially spaced-apart longitudinally extending tubular arms 67 having adjoined proximal and distal extremities or end portions 68 and 71. A plurality of electrodes 72, longitudinally spaced-apart between proximal and distal extremities 68 and 71, are carried by each elongate tubular arm 67 for engaging the wall of the heart.

More specifically, elongate tubular arms 67 are each formed from a suitable material such as plastic which is generally circular in cross section except for a flat longitudinally extending outer wall portion 73 facing outwardly from the center of basket assembly 66 (See FIGS. 3 and 5). Elongate tubular arms 67 are each formed with first or inner and second or outer lumens 76 and 77 which extend therethrough from proximal extremity 68 to distal extremity 71. First lumen 76 serves as an inflatable bore and is generally semi-circular in cross section; second lumen 77 is generally rectangular in cross section. A flex circuit strip 78 made of a suitable material such as Kapton is longitudinally disposed within outer lumen 77 and is provided with electrodes 72 spaced along the one side thereof facing outer wall portion 73 and leads 81 extending from the electrodes to one end of the flex circuit strip at proximal extremity 68. Elongate tubular arms 67 have an outer diameter ranging from 0.025 to 0.055 inches and inflatable lumen 76 has an inner diameter ranging from 0.023 to 0.053 inches. Electrodes 72 can be of any suitable configuration such as square or circular when viewed in plan and are shown as being generally square.

Elongate tubular arms 67 are extruded with two lumens therethrough, cross-linked using radiation and then expanded to an outer diameter in the range referred to above and an inner diameter in the range referred to above with respect to inflatable lumen 76. Flex circuit strip 78 is then disposed within outer lumen 77 through one end thereof with electrodes 72 on the flex circuit strip facing outwardly. With inflatable lumen 76 pressurized, elongate tubular arm 67 is heated so that nonpressurized outer lumen 77 shrinks around flex circuit strip 78 to secure the flex circuit strip therein and form flat outer wall portion 73. A suitable heat activated adhesive such as epoxy or silicone, not shown in the drawings, can be applied to the inside surface of flex circuit strip 78 for further securing the flex circuit strip within outer lumen 77. Longitudinally spaced-apart openings 82 in alignment with electrodes 72 are cut through outer wall portion 73 to permit access to the electrodes. Openings 82 are sized smaller than the surface of electrodes 72 to minimize corruption of the electrical signals carried by leads 81 from the other electrodes 72 on flex circuit strip 78. A plurality of longitudinally spaced-apart radiopaque markers or traces, not shown in the drawings, can be disposed in outer lumen 77 or otherwise carried by tubular arm 67 for the purposes discussed above with respect to mapping apparatus 21. The traces can have a width or diameter of approximately 0.003 inches and are surrounded by a suitable nonconductive material such as plastic to avoid corruption or interference with the signals detected and transmitted by electrodes 72 and leads 81 within outer lumen 77.

Figure 7:
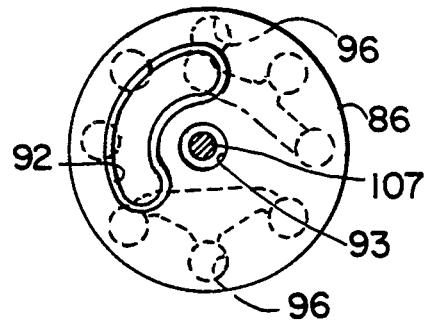
FIG. 7 is a cross-sectional view taken along the line 7—7 of FIG. 6.

Proximal extremities 68 of elongate tubular arms 67 are joined to a longitudinally extending cylindrical member or annulus 86 made of a suitable material such as plastic and mounted to distal extremity 56 of flexible elongate tubular member 52. Annulus 86 is included within the means carried by distal extremity 56 for interconnecting fluid conducting lumen 58 in flexible elongate tubular member 52 with at least certain of, and as shown in FIGS. 3, 6 and 7 all of, inflatable lumens 76 in elongate tubular arms 67. More specifically, annulus 86 is generally circular in cross-section and has an outer diameter substantially equal to the outer diameter of flexible elongate tubular member 52. Annulus has a first or upper end portion 87 and a second or lower end portion 88 with a connector 91 extending longitudinally therefrom and sized and positioned for snug disposition within fluid conducting lumen 58 of flexible elongate tubular member 52. A first bore or fluid conducting lumen 92 extends longitudinally through connector 91 into annulus 86 and communicates with fluid conducting lumen 58 and a second or central bore or lumen 93 extends through annulus 86 for alignment and communication with central lumen 57 when the annulus is mounted or secured to flexible elongate tubular member 52. A plurality of eight circumferentially disposed feeder bores or lumens 96 extend longitudinally through upper portion 87 and communicate with fluid conducting lumen 92 of annulus 86.

Annulus lower portion 88 can be joined to flexible elongate tubular member 52 by any suitable means known to those skilled in the art. Proximal extremities 68 of elongate tubular arms 67 can be similarly joined to annulus upper portion 87 so that arm inflatable lumens 76 communicate with respective annulus feeder lumens 96. Annulus 86 is also included in the means of catheter probe 51 for interconnecting leads 81 on flex circuit strips 78 carried within elongate tubular arms 67 with electrical conductors 97 carried within third lumen 61 and shown in FIG. 4.

Catheter probe 51 is provided with a triple arm connector 101 joined to proximal extremity 53 of flexible elongate tubular member 52. A suitable inflation device such as syringe 102 is mounted to connector 101 and is included within the means mounted on proximal extremity 53 to permit a pressurized liquid or other incompressible fluid to be introduced into fluid conducting lumen 58 of flexible elongate tubular member 52 and through annulus 86 into inflatable lumens 76 of tubular arms 67. A conventional electrical connector 103 is joined to triple arm connector 101 and electrically connected to electrical conductors 97 carried within third lumen 61 to permit attachment of catheter probe 51 to suitable data collection equipment for analyzing the electrical signals from electrodes 72 as accessible at electrical connector 103.

Distal extremities 71 of elongate tubular arms 67 are heat joined to form a tip 106 which serves as the distal end or tip of basket assembly 66 and is included within the interconnecting means of catheter probe 51 for connecting tubular arm distal extremities 71. As so interconnected, elongate tubular arms 67 have the capability and tend to bow outwardly when inflatable lumens 76 therein are filled with a pressurized liquid by syringe 102. An elongate element or pull wire 106 formed of a suitable material such as stainless steel and having a diameter ranging from 0.005 to 0.020 inches slidably extends through central lumen 57 of flexible elongate tubular member 52 and central lumen 93 of annulus 86. Pull wire 107 has a first or distal end 108 joined or connected to tip 106 and a second or proximal end 111 accessible at proximal extremity 53 of flexible elongate tubular member 52. Pull wire 107 is included within the means of catheter probe 51 for varying the configuration of expanded basket assembly 66 and is provided with a knob 112 on its proximal extremity for operation thereof.

Figure 8:
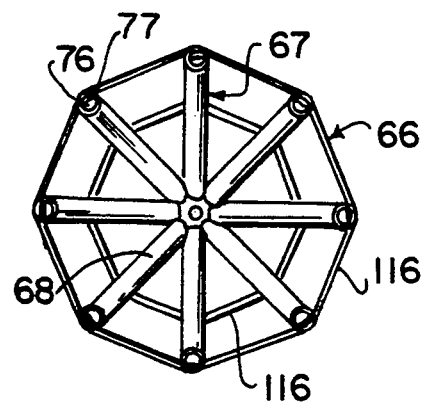
FIG. 8 is a cross-sectional view taken along the line 8—8 of FIG. 3.
Figure 9:
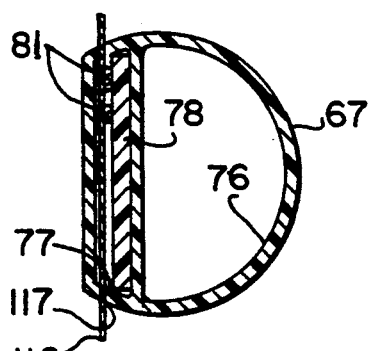
FIG. 9 is a cross-sectional view taken along the line 9—9 of FIG. 3.

Spacing means, which includes flexible members or fibers 116, is included within catheter probe 51 for establishing a desired substantially uniform circumferential spacing between elongate tubular arms 67 of expanded basket assembly 66 (See FIGS. 3, 8 and 9). Fibers 116 are coupled and secured to elongate tubular arms 67 and are configured on basket assembly 66 in substantially the same manner that fibers 46 are configured on basket assembly 28 of mapping apparatus 21. A plurality of transversely aligned first and second bores 117 extend from the outer surface of elongate tubular arms 67 into outer lumen 77 thereof and are included in the means for securing fibers 116 to the elongate tubular arms. Fibers 116 extend through bores 117, as shown in FIG. 9, and can be further secured to elongate tubular arms 67 by a suitable adhesive. As so mounted, fibers 116 form a plurality of rings spaced longitudinally between proximal and distal extremities 68 and 71 of elongate tubular arms 67.

In operation and use, basket assembly 66 of catheter probe 51 is inserted into a chamber of the heart, such as a ventricle, in substantially the same manner as discussed above with respect to basket assembly 28 of mapping apparatus 21 for mapping the wall of a chamber of the heart. Once the guiding catheter has been pulled back through the aortic valve to expose basket assembly 66 therein, syringe 102 can be used to expand the basket assembly with a suitable liquid or other incompressible fluid having a pressure ranging from 50 to 150 psi. The pressurized liquid travels from syringe 102 through fluid conducting lumens 58 and 92 in flexible elongate tubular member 52 and annulus 86, respectively, into inflatable lumens 76 in elongate tubular arms 67 to cause elongate tubular arms 67 to bow outwardly from the center of basket assembly 66. An aqueous saline solution is a suitable liquid for pressurizing basket assembly 66. Alternatively, however, a radiopaque fluid such as that used for angioplasty could be used for pressurizing basket assembly 66. Such a fluid would make basket assembly 66 more easily visible to fluoroscopic viewing.

Pull wire proximal end 111 can be retracted from flexible elongate tubular member 52 to cause elongate tubular arms 67 of basket assembly 66 to form an ovoid-like structure or configuration so that electrodes 72 substantially engage the endocardium of the ventricle for mapping electrical impulses therein. Pull wire 107 permits variations in the configuration of expanded basket assembly 66 to accommodate the configuration of the wall of the heart engaged by elongate tubular arms 67. In this regard, pull wire proximal end 111 can be moved inwardly or outwardly of central lumen 57 in flexible elongate tubular member 52 to move pull wire distal end 108 joined to tip 106 with respect to distal extremity 56 of the flexible elongate tubular member and change the shape of bowing elongate tubular arms 67. As pull wire distal end 108 approaches tubular member distal extremity 56, the outward bow of elongate tubular arms 67 increases. Syringe 102 permits variation in the pressure of the fluid within inflatable lumens 76 as a further means for adjusting the configuration of basket assembly 66 within the ventricle and the engagement of electrodes 72 with the wall of the heart. Fibers 116 act similar to fibers 46 of mapping apparatus 21 to prevent one elongate tubular arm 67 from pulling apart from an adjacent elongate tubular arm more than a predetermined distance.

If rotation of basket assembly 66 is deemed necessary to obtain the desired mapping, syringe 102 can be used to deflate elongate tubular arms 67 and reinflate the elongate tubular arms once the contracted basket assembly is rotated. Upon completion of the endocardial mapping, elongate tubular arms 67 are deflated so that upon full extension of pull wire 107 the guiding catheter can be pushed back through the aortic valve to completely cover contracted basket assembly 66. Catheter probe 51 can then be slid out of the guiding catheter and taken out of the body of the patient.

The fluid activated expansion means of basket assembly 66 eliminates the possibility of undesirable fibrillations of the heart which may result from electrically activated expansion means heretofore provided. In addition, the minimal mechanical resistance of elongate tubular arms 67 when deflated enhances the ability of catheter probe 51 to navigate the tortuosities of the patient's microcirculatory system when being positioned therein.

It should be appreciated that an endocardial mapping apparatus having elongate flexible tubular arms which are inflatable can be provided without interconnecting flexible cross members. For example, a catheter probe substantially identical to catheter probe 51 but not including flexible fibers 116 would be within the scope of the present invention. The absence of flexible cross members would further decrease the mechanical resistance of the probe's basket assembly and further facilitate insertion and extraction of the catheter probe from the microcirculatory system of the patient.

Figure 10:
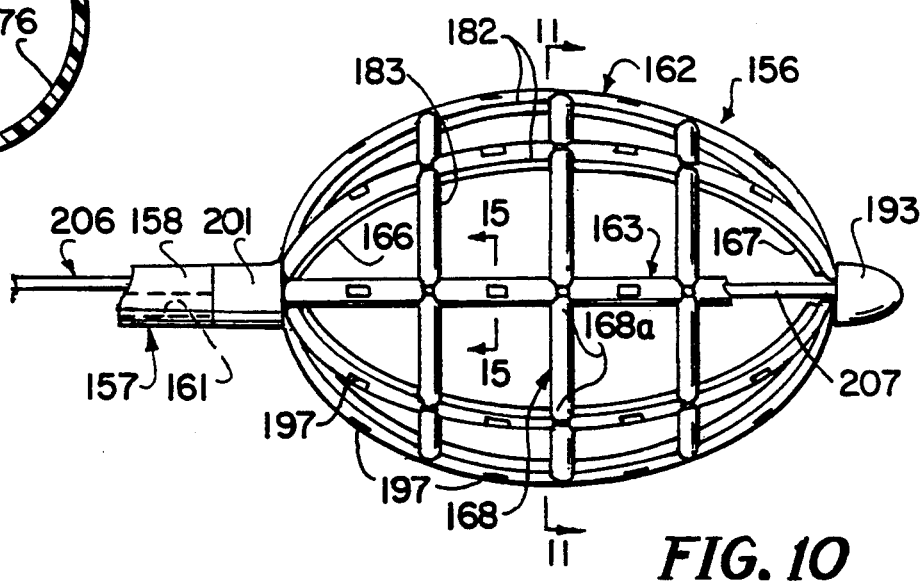
FIG. 10 is a side elevational view, partially broken away, of a portion of another embodiment of the endocardial mapping apparatus of the present invention.
Figure 11:
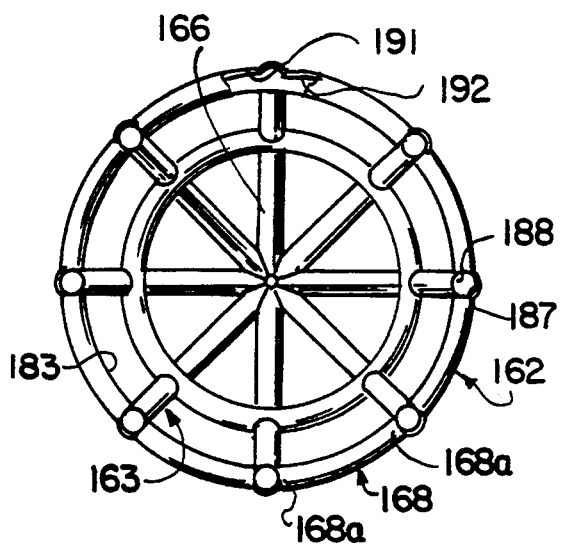
FIG. 11 is a cross-sectional view taken along the line 11—11 of FIG. 10.
Figure 15:
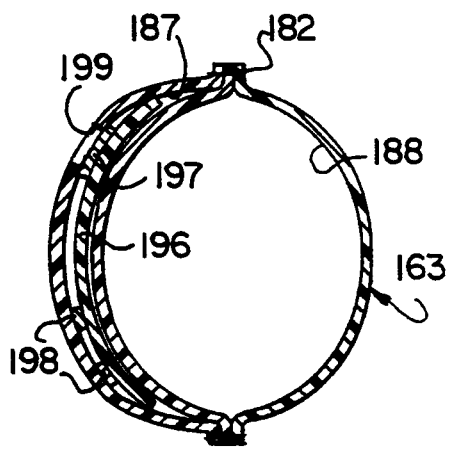
FIG. 15 is a cross-sectional view taken along the line 15—15 of FIG. 10.

In another embodiment of the mapping apparatus of the present invention, a catheter probe 156 having both inflatable arms and cross members and illustrated in FIGS. 10, 11 and 15 is provided. Catheter probe 156 is substantially similar to catheter probe 51 and includes a flexible elongate tubular member 157, substantially identical to flexible elongate tubular member 52, having a proximal extremity not shown in the drawings and an opposite distal extremity 158. Flexible elongate tubular member 157 includes a first or fluid conducting lumen 161, shown in part in FIG. 10, extending from the proximal extremity to distal extremity 158. A basket assembly 162 is secured in a fixed position to distal extremity 158 of flexible elongate tubular member 157 and is moveable between contracted and expanded conditions substantially similar to that shown in FIG. 3 with respect to catheter probe 51.

Figure 12:
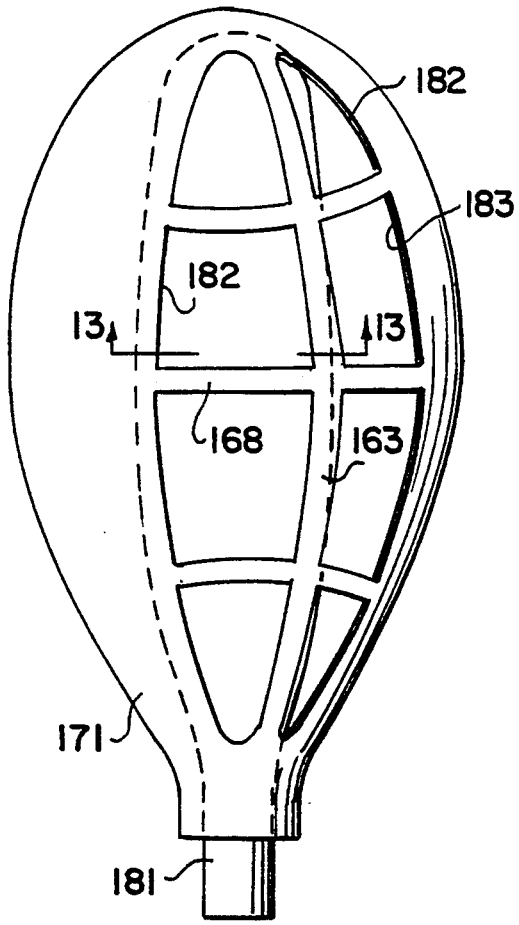
FIG. 12 is an enlarged plan view of the balloons used to form the basket assembly shown in FIG. 10.
Figure 13:
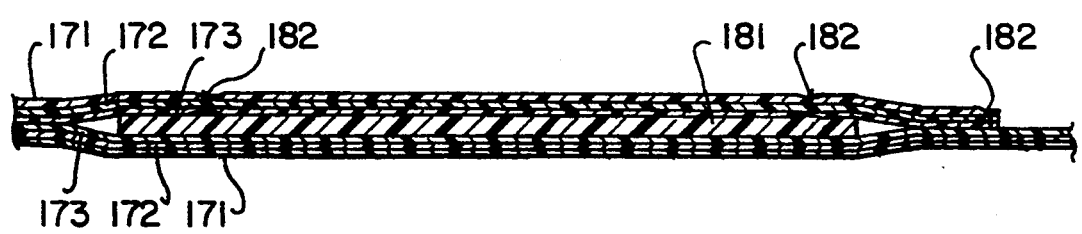
FIG. 13 is a cross-sectional view taken along the line 13—13 of FIG. 12.
Figure 14:
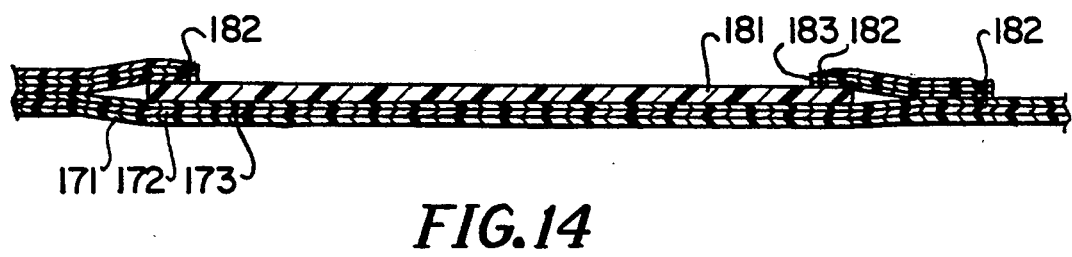
FIG. 14 is a cross-sectional view, similar to FIG. 13, of the balloons used to form the basket assembly shown in FIG. 10.

Basket assembly 162 is comprised of a plurality of elongate flexible tubular arms 163 having respective proximal and distal extremities 166 and 167 and a plurality of interconnecting flexible members in the form of inflatable tubular cross members 168 formed integral with the flexible tubular arms. Basket assembly 162 is formed from first, second and third balloons 171, 172 and 173 as generally shown in FIGS. 12-14. Balloons 171, 172 and 173 are each made from a suitable material such as polyethylene and are generally ovoid in shape and sized so that second balloon 172 can be disposed within first balloon 171 and third balloon 173 disposed within second balloon 172. Once second and third balloons 172 and 173 are so disposed within first balloon 171, a thin separator sheet 181 made of any suitable material such as teflon is inserted within the opening at the bottom of third balloon 173 and a heated pattern forming a plurality of continuous and closed interconnecting bonds or seams 182 is pressed or stamped against the separator sheet and the portions of the balloons thereabove. The portions of balloons 171, 172 and 173 circumscribed by interconnecting seams or seals 182 are cut out to form openings 183 through one surface of the balloons.

In FIGS. 12 and 13, one set of vertically aligned interconnecting seams 182 and openings 183 formed therefrom are shown in balloons 171, 172 and 173 and a second set of interconnecting seams 182 formed in the balloons adjacent to the first set and overlying separator sheet 181 are shown. In FIG. 14, the portion of balloons 171, 172 and 173 circumscribed by the second set of interconnecting seams 182 have been removed to form a second set of openings 183 in the balloons. In this manner, sets of adjacent longitudinally disposed interconnecting seams 182 serve to form a flexible and inflatable tubular arm 163 with first and second lumens 187 and 188 extending from arm proximal extremity 166 to arm distal extremity 167. Sets of latitudinally disposed interconnecting seams 182 serve to form an inflatable tubular cross member 168 with end portions 168a adjoining respective adjacent flexible tubular arms 163 and first and second lumens 191 and 192 in communication with respective first and second lumens 187 and 188 of the adjoining flexible tubular arms (See FIG. 11).

The tops of balloons 171, 172 and 173 are then heat joined so first and second lumens 187 and 188 of each flexible tubular arm 163 are closed off and a bulbous tip 193 is molded or otherwise formed thereon in a manner known to those skilled in the art. Tip 193 and balloons 171, 172 and 173 are included within the interconnecting means provided in catheter probe 156 for connecting distal extremities 167 of tubular arms 163. The bottoms of balloons 171, 172 and 173 are cut off so that proximal extremity 166 of each flexible tubular arm 163 is separated from the adjacent flexible tubular arms.

Once the flexible tubular arms, tubular cross members and lumens of basket assembly 162 has been so formed, a flex circuit strip 196, substantially identical to flex circuit strip 78 and having electrodes 197 and leads 198 provided on one side thereof, can be inserted into first lumen 187 of each flexible tubular arm 163 and secured therein by heat shrinking and/or an adhesive in the manner discussed above with respect to catheter probe 51. Openings 199 sized smaller than the surface of electrodes 197 are cut through first balloon 171 to permit access to the electrodes. Radiopaque markers or traces, not shown in the drawings, are selectively positioned within first lumens 187 to permit fluoroscopic viewing of basket assembly as also discussed above.

Basket assembly 162, with flex circuit strips 196 mounted in flexible tubular arms 163 thereof, is then mounted and joined to a longitudinally extending cylindrical member or annulus 201 substantially similar to annulus 86 and mounted to distal extremity 158 of flexible elongate tubular member 157. In this manner, second or inflatable bores or lumens 188 and 192 of basket assembly 162 are in communication with fluid conducting lumen 161 of flexible elongate tubular member 157. Annulus 201 is included within the means carried by distal extremity 158 for interconnecting fluid conducting lumen 161 within flexible elongate tubular member 157 with at least certain of, and as described all of, inflatable lumens 188 within tubular arms 163. In addition, annulus 201, together with inflatable lumen 188, serve as means carried by distal extremity 158 for interconnecting fluid conducting lumen 161 with inflatable lumens 192 of tubular cross members 168. Opposite end portions 168a of inflatable tubular cross members 168 are included within the means establishing communication between inflatable lumens 188 within flexible tubular arms 163 and inflatable lumens 192 within tubular cross members 168.

Catheter probe 156 has electrical conductors, not shown in the drawings, carried by flexible elongate tubular member 157 which are substantially similar to electrical conductors 97 of catheter probe 51. Annulus 201 is included in the means of catheter probe 156 for interconnecting leads 198 on flex circuit strips 196 carried within flexible tubular arms 163 with the electrical conductors carried by flexible elongate tubular member 157.

Catheter probe 156 includes a pull element or wire 206, substantially identical to pull wire 107, extending through flexible elongate tubular member 157 and annulus 201 and having a first or distal end 207 connected or joined to tip 193. Pull wire 107 is included within the means for varying the configuration of basket assembly 162 in the same manner as discussed above with respect to pull wire 107 and basket assembly 66.

A three arm connector, syringe and electrical connector, not shown in the drawings but substantially identical to three arm connector 101, syringe 102 and electrical connector 103 discussed above with respect to catheter probe 51, are included within catheter probe 156 and are mounted to the proximal extremity of flexible elongate tubular member 157. The syringe can serve as means for introducing a pressurized aqueous saline solution or other suitable liquid or incompressible fluid into fluid conducting lumen 161 of flexible elongate tubular member 157 to inflate flexible tubular arms 163 and tubular cross members 168.

In operation and use, basket assembly 162 of catheter probe 156 can be introduced into a ventricle of the heart in substantially the same manner as discussed above with respect to catheter probe 51. Once so disposed within the heart, flexible tubular arms 163 and tubular cross members 168 can be inflated with the pressurized aqueous saline solution. When inflated, inflatable lumens 188 and 192 are each generally circular in cross-section as shown in FIG. 15 with respect to inflatable lumen 188. Inflated tubular arms 163 have the capability to bow outwardly to form an ovoid-like structure so that electrodes 197 carried thereby substantially engage the endocardium to map the electrical impulses therein.

Tubular cross members 168 integrally coupled to flexible tubular arms 163 and extending therebetween are included within the spacing means of catheter probe 156 for establishing a desired substantially uniform circumferential spacing between the flexible tubular arms of expanded basket assembly 162. In addition, end portions 168a of tubular cross members 168 permit inflatable lumens 192 in the tubular cross members to be inflated when inflatable lumens 188 in flexible tubular arms 163 are inflated. Tubular cross members 168 extend at an angle with respect to flexible tubular arms 163 and, more specifically, are aligned at substantially right angles with respect to the flexible tubular arms. Tubular cross members 168 serve the dual function of preventing one flexible tubular arm 163 from pulling apart from an adjacent flexible tubular arm more than a predetermined distance and of inhibiting a flexible tubular arm 163 from moving toward an adjacent flexible tubular arm. Openings 183 permit blood to flow basket assembly 162 during mapping. The configuration of expanded basket assembly 162 can be varied by moving pull wire 206 so that distal end 207 thereof and tip 193 attached thereto are moved toward or away from distal extremity 158 of flexible elongate tubular member 157.

In view of the foregoing, it can be seen that a new and improved endocardial mapping apparatus which maintains substantially uniform circumferential spacing of the electrodes on the distal end thereof during endocardial mapping has been provided. A plurality of radially and longitudinally spaced electrodes are provided in a basket assembly which permits blood to flow therethrough during endocardial mapping. The array of electrodes is expanded into engagement with the wall of the chamber of the heart and is maintained in engagement with that wall during pumping action of the heart. The basket assembly thereof is formed from a plurality of circumferentially spaced-apart arms having minimal mechanical resistance for permitting them to travel through tortuosities within the microcirculatory system of the patient.

What is claimed is:

1. Apparatus for mapping a wall of a chamber of a heart having blood therein comprising a flexible elongate member having proximal and distal extremities and at least one lumen extending therethrough, a basket assembly carried by the distal extremity of the flexible elongate member and being movable between contracted and expanded positions, the basket assembly having a plurality of elongate longitudinally-extending flexible circumferentially spaced-apart arms with proximal and distal extremities, a plurality of longitudinally spaced-apart electrodes carried by each arm for engaging the wall of the heart and spacing means coupled to the arms at locations between the proximal and distal extremities of the arms for establishing a predetermined circumferential spacing between the arms when the basket assembly is in an expanded position in engagement with the wall of the heart, the spacing means having openings therebetween through which blood can flow.

2. Apparatus for mapping a wall of a chamber of a heart having blood therein comprising a flexible elongate member having proximal and distal extremities and at least one lumen extending therethrough, a basket assembly carried by the distal extremity of the flexible elongate member and being movable between contracted and expended positions, the basket assembly having a plurality of elongate longitudinally-extending flexible circumferentially spaced-apart arms with proximal and distal extremities, a plurality of longitudinally spaced-apart electrodes carried by each arm for engaging the wall of the heart and spacing means coupled to the arms and extending between the arms for establishing a predetermined circumferential spacing between the arms when the basket assembly is in expanded position in engagement with the wall of the heart, the spacing means having openings therebetween through which blood can flow and including flexible members attached to the arms for preventing one arm from pulling apart from an adjacent arm more than a predetermined distance.

3. Apparatus as in claim 2 wherein said flexible members are fibers.

4. Apparatus as in claim 2 wherein said flexible members are inflatable tubular members extending at an angle with respect to said elongate flexible arms and wherein said apparatus further comprises means for inflating the tubular members to inhibit one arm from moving toward an adjacent arm.

5. Apparatus as in claim 4 wherein said inflatable tubular members are aligned at substantially right angles with respect to said elongate flexible arms when said basket assembly is in its expanded position.

6. Apparatus as in claim 2 wherein said flexible members are attached to said elongate flexible arms in a plurality of locations spaced longitudinally between the proximal and distal extremities of the arms.

7. Apparatus for mapping a wall of a chamber of a heart having blood therein comprising a flexible elongate member having proximal and distal extremities and a fluid conducting lumen extending therethrough, a basket assembly carried by the distal extremity of the flexible elongate member and being movable between contracted and expanded conditions, the basket assembly comprising a plurality of elongate longitudinally-extending flexible inflatable arms having proximal and distal extremities and lumens therein, a plurality of spaced-apart electrodes carried by the arms for engaging the wall of the heart, means carried by the distal extremity of the flexible elongate member for interconnecting the fluid conducting lumen in the flexible elongate member with at least certain of the lumens in the arms and fluid introduction means mounted on the proximal extremity of the flexible elongate member for permitting fluid having a pressure to be introduced into the fluid conducting lumen of the flexible elongate member and thereby into the lumens of the arms.

8. Apparatus as in claim 7 wherein said inflatable arms are formed to bow outwardly when inflated to form an ovoid-like structure and to move said basket assembly to an expanded condition.

9. Apparatus as in claim 8 further comprising interconnecting means for connecting the distal extremities of said inflatable arms and variation means for varying the configuration of said basket assembly to accommodate the configuration of the wall of the heart engaged by the arms.

10. Apparatus as in claim 9 wherein said variation means includes a pull wire slidably extending through said flexible elongate member and having a first end connected to said interconnecting means and a second end accessible at the proximal extremity of the flexible elongate member to permit variations in the configuration of said basket assembly by moving the interconnecting means with respect to said distal extremity of the flexible elongate member to change the outward bowing of said inflatable arms.

11. Apparatus as in claim 7 further comprising spacing means coupled to said inflatable arms and extending circumferentially between the arms for establishing a predetermined circumferential spacing between the arms when said basket assembly is in an expanded condition and in engagement with the wall of the heart.

12. Apparatus as in claim 11 wherein said spacing means includes flexible members attached to said inflatable arms in a plurality of spaced-apart locations for preventing one arm from pulling apart from an adjacent arm more than a predetermined distance.

13. Apparatus as in claim 11 wherein said spacing means includes inflatable cross members extending at an angle with respect to said inflatable arms and having lumens therein and wherein said apparats further comprises means establishing communication between the lumens in the arms and the lumens in the cross members so that the cross members are inflated when the arms are inflated to inhibit one arm moving toward an adjacent arm.

14. Apparatus as in claim 7 wherein said fluid introduction means permits variation in the pressure of the fluid in the lumens of said inflatable arms.

15. Apparatus for mapping a wall of a chamber of a heart having blood therein comprising a flexible elongate member having proximal and distal extremities and a longitudinal axis, a basket assembly carried by the distal extremity of the flexible elongate member and being movable between contracted and expanded positions, the basket assembly having a plurality of elongate flexible circumferentially spaced-apart arms extending longitudinally of the longitudinal axis, the arms having proximal and distal extremities, a plurality of electrodes carried by each arm adapted to engage the wall of the heart and flexible members connected to the arms extending transversely of the arms and interconnecting the arms at locations between the proximal and distal extremities of the arms, the transversely extending flexible members being relatively inextensible so that the transversely extending flexible members serve to establish a maximum circumferential spacing between adjacent arms when the basket assembly is moved toward an expanded position in engagement with the wall of the heart.

* * * * *